United States Patent [19]
Kajiji et al.

[11] Patent Number: 4,962,048
[45] Date of Patent: Oct. 9, 1990

[54] MONOCLONAL ANTIBODIES TO HUMAN PANCREATIC CANCER

[75] Inventors: Shama Kajiji, San Diego; Vito Quaranta, La Jolla, both of Calif.

[73] Assignee: Scripps Clinic & Research Foundation, La Jolla, Calif.

[21] Appl. No.: 333,848

[22] Filed: Apr. 3, 1989

Related U.S. Application Data

[63] Continuation of Ser. No. 16,552, Feb. 19, 1987, abandoned.

[51] Int. Cl.⁵ .................. G01N 33/53; C12N 15/00
[52] U.S. Cl. .................... 436/548; 435/172.2; 435/240.27; 530/387; 530/808; 530/809
[58] Field of Search .............. 436/548; 424/9.85; 435/172.2, 240.27; 530/357

[56] References Cited
U.S. PATENT DOCUMENTS 4,444,744  4/1984  Goldenberg ................. 424/85
4,485,093  11/1984  Runge ........................ 424/85
4,664,911  5/1987  Uhr et al. .................... 424/85

OTHER PUBLICATIONS

Schmiegel et al., *Cancer Research,* vol. 45, pp. 1402–1407 (Mar. 1985).
Kohler et al., *Nature,* vol. 256, pp. 495–497 (Aug. 1975).
Akiyama et al., *Chemical Abstracts,* vol. 106:100759e (1987).

*Primary Examiner*—Robert J. Warden
*Assistant Examiner*—Janelle Graeter
*Attorney, Agent, or Firm*—Irell & Manella

[57] ABSTRACT

Novel hybridoma cell lines producing monoclonal antibodies which react specifically with human pancreatic cancer cells are described. Methods for producing antigenic preparations to generate the hybridoma cell lines and for selecting, purifying and characterizing the monoclonal antibodies reactive with human cells, including pancreatic cancer cells, are disclosed.

10 Claims, 13 Drawing Sheets

REACTIVITY[a] OF MONOCLONAL ANTIBODIES WITH FRESH FROZEN HUMAN TUMOR TISSUE SECTIONS BY IMMUNOPEROXIDASE STAINING

| Cell lines (ATTC No.) | HB 9318 | HB 9319 |
|---|---|---|
| Pancreatic Cancer | | |
| -ductal adenocarcinoma | -[b] | 2+ |
| | 2+[b] | 1+ |
| | 2+[b] | 4+ |
| | - | 1 |
| | 4+[b] | 1+ |
| | 3+[b] | 3+ |
| | 4+ | 4+ |
| -islet cell Cancer/insulinoma | - | - |
| | - | 1+ |
| -acinar cell Cancer | - | 3+ |
| Oral Squamous Cancer | 1[b] | 3+ |
| | 1[b] | 4+ |
| | - | 2+ |
| | -[b] | 4+ |
| Adenoid Cystic Cancer | 3+ | 2+ |
| Salivary Gland Cancer | 4+[b] | 3+ |
| Esophageal Cancer | 3+[b] | 3+ |
| Gastric Cancer | 3+[b] | 3+ |
| | 2+ | 4+ |
| | 3+ | 3+ |
| | 1+[b] | 3+ |
| Colon Cancer | 3+[b] | 3+ |
| | -[b] | 1+ |
| | 3+ | 3+ |
| | 3+[b] | 4+ |

FIG. 3-1

|  | HB 9318 | HB 9319 |
|---|---|---|
| Hepatoma | - | 2+ |
|  | - | 2+ |
| Laryngeal Cancer | 2+[b] | 4+ |
|  | 2+[b] | 3+[b] |
| Melanoma | 1+[b] | 4+ |
|  | - | 4+ |
|  | - | 4+ |
| Sarcoma | - | 4+ |
|  | - | 4+ |
| Lung Cancer |  |  |
| -adenocarcinoma | 1+ | 1+ |
|  | - | 3+ |
|  | - | 1+ |
| -squamous Cancer | 1+[b] | 3+ |
|  | - | 2+ |
|  | - | 3+ |
|  | - | 3+ |
|  | - | 3+ |
| -adenosquamous | 1+[b] | 3+ |
| -oat cell Cancer | - | - |
|  | - | - |
| -large cell Cancer | 4+ | 4+ |
| -Mesothelioma | - | 1+ |

FIG. 3-2

|  | HB 9318 | HB 9319 |
|---|---|---|
| Breast Cancer | - | 3+ |
|  | - | 4+ |
|  | - | 3+ |
|  | - | 2+ |
|  | 1+ | 2+ |
| Cervical Cancer | 2+[b] | 1+ |
|  | 1+ | 4+ |
| Endometrial Cancer | - | 3+ |
|  | - | 4+ |
|  | 3+[b] | 2+ |
| Ovarian Cancer | - | 4+ |
|  | - | 3+ |
|  | 3+[b] | 2+ |
| Prostatic Cancer | 1+[b] | 4+ |
| Bladder Cancer | 1+[b] | 2+ |
|  | 3+[b] | 2+[b] |
| Kidney Cancer | - | 4+ |
|  | 2+ | - |

[a]Intensity of staining was scored from 1 to 4+ with 4+ indicating greatest intensity and with "-" indicating lack of staining.

[b]Basement membrane staining.

FIG. 3-3

ELISA REACTIVITY OF MONOCLONAL ANTIBODIES WITH CULTURED HUMAN CELLS

| Cell lines (ATCC NO.) | HB 9318 | HB 9319 |
|---|---|---|
| Pancreatic Cancer | | |
| Colo 357[a] | 3+ | 2+ |
| FG[a] | 3+ | 3+ |
| SG[a] | 3+ | 3+ |
| FG-Met-2[a] | 4+ | 4+ |
| KWP-1[a] | 4+ | 2+ |
| RWP-2[a] | 3+ | 1+ |
| PANC-1 (CRL 1469) | 3+ | 2+ |
| ASPC-1 (CRL 1682) | 3+ | 1+ |
| Hs 766T (HTB 134) | 4+ | 1+ |
| BxPC-3 (CRL 1687) | 4+ | 4+ |
| Lung Cancer | | |
| -adenocarcinoma | | |
| UCLA-P3[b] | - | 2+ |
| A549 (CCL 185) | 2+ | 1+ |
| CALU 6 (HTB 56) | - | 4+ |
| -squamous cancer | | |
| T-222[b] | 2+ | 4+ |
| SK-MES-1 (HTB 58) | 3+ | 3+ |
| CALU-1 (HTB 54) | 2+ | 3+ |
| USCLS-1[b] | 3+ | 3+ |
| -oat cell Cancer | | |
| T-293[c] | - | 1+ |
| NCI-H69 (HTB 119) | - | - |

FIG. 4-1

| Cell lines (ATCC NO.) | HB 9318 | HB-9319 |
|---|---|---|
| Breast Cancer | | |
|     734B[d] | - | 3+ |
|     BT-20 (HTB 19) | 3+ | 4+ |
|     MDA-MB-435S (HTB 129) | - | 3+ |
| Bladder Cancer | | |
|     T24 (HTB 4) | - | 2+ |
|     J82 (HTB 1) | - | 2+ |
|     5637 (HTB 9) | 2+ | 3+ |
| Cervical Cancer | | |
|     ME-180 (HTB 33) | 3+ | 4+ |
| Prostatic Cancer | | |
|     DU-145 (HTB 43) | 2+ | 3+ |
| Pharyngeal Cancer | | |
|     FaDu (HTB 43) | 3+ | 4+ |
| Skin Cancer | | |
|     A-431 (CRL 1555) | 3+ | 3+ |
| Colon Cancer | | |
|     COLO 396[d] | 4+ | 4+ |
| Hepatoma | | |
|     SK-HEP-1 (HTB 52) | 3+ | 2+ |
| Mesodermal Tumor | | |
|     SK-UT 1 (HTB 114) | - | 2+ |

FIG. 4-2

| Cell lines (ATTC NO.) | HB 9318 | HB 9319 |
| --- | --- | --- |
| Melanoma | | |
|     ML-873-1[c] | - | 2+ |
|     WM239A[c] | - | 3+ |
|     WM2664 (CRL 1676) | - | 3+ |
|     A-375P[c] | - | 4+ |
|     A375M[c] | - | 3+ |
|     M14[c] | - | 3+ |
|     M21[c] | - | 4+ |
|     MS-1[c] | - | 3+ |
|     FOSS[c] | - | 3+ |
|     Melur[c] | - | 3+ |
| Glioblastoma | | |
|     U38MG (HTB 1c) | - | 1+ |
|     U87MB (HTB 14) | - | 3+ |
|     U-373MG (HTB 17) | - | 3+ |
| Neuroblastoma | | |
|     SK-N-SH (HTB 11) | - | 2+ |
|     SK-N-MC (HTB 10) | - | - |
|     LAN-1[c] | 2+ | 1+ |
| B-Lymphoblastoid | | |
|     L14[b] | - | 1+ |
|     LG-2[b] | - | 1+ |
|     721-P[e] | - | - |
|     GM3107[b] | - | 2+ |

FIG. 4-3

| Cell lines (ATCC NO.) | HB 9318 | HB 9319 |
|---|---|---|
| T-Lymphoblastoid | | |
|     MOLT-4 (CRL 1582) | - | - |
|     HPB-ALL[b] | - | 2+ |
|     HSB-2[d] | - | - |
| Promyelocytic Leukemia | | |
|     HL-60 (CCL 240) | - | - |
| Erythroleukemia | | |
|     K562 (CCL 243) | - | - |
| Diploid Fibroblast | | |
|     WI-38 (CCL 75) | - | - |
| Human RBC | - | - |

Cell lines were obtained as follows:

a. P. Meitner, Department of Medicine, Brown University b. L. Walker, Department of Immunology, Scripps Clinic and Research Foundation c. R. Reisfeld, Department of Immunology, Scripps Clinic and Research Foundation d. T. Edginton, Department of Immunology, Scripps Clinic and Research Foundation e. F. Bach, University of Minnesota

FIG. 4-4

REACTIVITY OF MONOCLONAL ANTIBODIES WITH

FRESH FROZEN NON-MALIGNANT PATHOLOGIC HUMAN TISSUE

SECTIONS BY IMMUNOPEROXIDASE STAINING

| Cell lines (ATCC NO.) | HB 9318 | | HB 9319 | |
|---|---|---|---|---|
| Pancreas (chronic pancreatitis) | | | | |
|     acini | - | - | - | - |
|     ducts | 2+ | -[b] | 2+ | 1+ |
|     islets of Langerhans | - | - | - | - |
| Pancreas (SLE)[a] | | | | |
|     acini | - | | 4+ | |
|     ducts | -[b] | | - | - |
|     islets of Langerhans | - | | - | |
| Uterus (leiomyoma) | - | - - - | 3+ 4+ | 4+ 4+ |
| Ovary (fibroadenoma) | - | | 2+ | |
| Endometrium (hyperplastic) | 3+ | | 4+ | |
| Prostate (hyperplastic) | | | | |
|     upper layers of epithelium | - | | 3+ | |
|     basal layers of epithelium | 4+ | | 3+ | |
|     basement membrane | 4+ | | - | |

[a]SLE, Systemic Lupus Erythematosus

[b]Basement membrane staining

FIG. 5

REACTIVITY OF MONOCLONAL ANTIBODIES

WITH FRESH FROZEN NORMAL HUMAN TISSUE

SECTIONS BY IMMUNOPEROXIDASE STAINING

| Cell lines (ATCC NO.) | HB 9318 | HB 9319 |
|---|---|---|
| Esophagus | | |
| stratified squamous epithelium | | |
| -upper layers | - | 3+ |
| -basal layers | 4+ | 4+ |
| basement membrane | 4+ | - |
| Stomach | | |
| gastric pits | - | 3+ |
| gastric glands | | |
| -parietal cells | - | 2+ |
| -chief cells | - | 2+ |
| lamina propria | - | 1+ |
| Small Intestine | | |
| jejunal epithelium | - | 2+ |
| ileal epithelium | 3+ | 3+ |
| basement membrane | 4+ | - |
| Large Intestine | | |
| colonic epithelium | - | 1+ |
| crypts of Lieberkuhn | - | 1+ |
| basement membrane | 4+ | - |
| lamina propria | - | 1+ |
| Liver | | |
| parenchyma | - - - | - 3+ - |
| bile ducts | - 1+ - | - 3+ - |

FIG. 6-1

|  | HB 9318 | HB 9319 |
|---|---|---|
| Pancreas (adult) | | |
| acini | - - - - | 4+ 4+ 4+ 4+ |
| ducts | - - -±- | - - - - |
| islets of Langerhans | - - - - | - - - - |
| Pancreas (fetal) | | |
| acini | - | 4+ |
| ducts | -± | 4+ |
| islets of Langerhans | - | - |
| Thymus | | |
| cortex | - | - |
| medulla | - | - |
| Lymph node | | |
| nodules | - | - |
| germinal centers | - | ±+ |
| Spleen | | |
| white pulp | - | - |
| red pulp | - | 1+ 1+ |
| Kidney (adult) | | |
| glomeruli | - - - | - - - |
| proximal tubules | - - - | - - - |
| distal tubules | - - - | - - - |
| Kidney (fetal) | | |
| glomeruli | - | 3+ |
| proximal tubules | 1+ | 3+ |
| distal tubules | - | 3+ |

FIG. 6-2

|  | HB 9318 | HB 9319 |
|---|---|---|
| Cervix | | |
| columnar epithelium | - 1+ | 4+ 3+ |
| -basement membrane | 4+ 4+ | - - |
| squamous epithelium | | |
| -upper layers | - - | 2+ 3+ |
| -basal layers | 4+ 4+ | 4+ 4+ |
| -basement membrane | 4+ 4+ | - - |
| Uterus | | |
| endometrium | 1+ - | 3+ 2+ |
| myometrium | - - | 4+ 2+ |
| Ovary | | |
| cortex | - | - |
| medulla | - | - |
| Breast | | |
| lobule | 4+ 2+ | 4+ 4+ |
| duct | 4+ 3+ | 4+ 4+ |
| basement membrane | 4+ 4+ | 4+ 4+ |
| Lung (adult) | | |
| parenchyma | - - - | ?+ 2+ - |
| Lung (fetal) | | |
| parenchyma | - | 2+ |
| Thyroid | | |
| epithelial cells | - | 1+ |
| colloid | - | - |

FIG. 6-3

|  | HB 9318 | HB 9319 |
|---|---|---|
| Cerebrum |  |  |
|   cortex | - | 3+ |
| Cerebellum |  |  |
|   granular layer | - | - |
|   molecular layer | - | 2+ |
|   Purkinje cells | - | 2+ |
| Plantar skin |  |  |
|   stratum corneum | - | 3+ |
|   stratum granulosum | - | 3+ |
|   stratum spinosum | 1+ | 3+ |
|   stratum germinativum | 3+ | 4+ |
|   basement membrane | 4+ | 4+ |

[a]Basement membrane staining

FIG. 6-4

MONOCLONAL ANTIBODIES TO HUMAN PANCREATIC CANCER

This application is a continuation of application Ser. No. 16,552, filed Feb. 19, 1987, now abandoned.

BACKGROUND OF THE INVENTION

The present invention relates generally to novel hybridoma cell lines, and more specifically to monoclonal cell lines producing monoclonal antibodies reactive with human pancreatic cancer cells.

Cancer currently constitutes the second most common cause of death in the United States. Carcinomas of the pancreas are the eighth most prevalent form of cancer and fourth among the most common causes of cancer deaths in this country. The incidence of pancreatic cancer has been increasing steadily in the past twenty years in most industrialized countries, exhibiting the characteristics of a growing epidemiological problem.

The prognosis for pancreatic carcinoma is, at present, very poor, it displays the lowest five-year survival rate among all cancers. Such prognosis results primarily from delayed diagnosis, due in part to the fact that the early symptoms are shared with other more common abdominal ailments. The diagnosis of pancreatic cancer is often dependent on exploratory surgery, inevitably performed after the disease has advanced considerably.

Substantial efforts have been directed to developing tools useful for early diagnosis of pancreatic carcinomas. Nonetheless, a definitive diagnosis is often dependent on exploratory surgery which is inevitably performed after the disease has advanced past the point when early treatment may be effected. One promising method for early diagnosis of various forms of cancer is the identification of specific biochemical moieties, termed antigens present on the surface of cancerous cells. Antibodies which will specifically recognize and bind to the antigens present on the surfaces of cancer cells potentially provide powerful tools for the diagnosis and treatment of the particular malignancy. Tumor specific cell surface antigens have previously been identified for certain melanomas, lymphomas malignancies of the colon and reproductive tract.

There thus exists a great and long-felt need for a cell surface marker which is present on the surface of neoplastic cells of the pancreas, and for antibodies which specifically recognize such a cell surface marker. Such markers and corresponding antibodies would be useful not only in the early detection of pancreatic cancers, but in their treatment as well. The present invention satisfies these needs and provides related advantages as well.

SUMMARY OF THE INVENTION

The present invention provides monoclonal antibodies characterized in that the antibodies react specifically to human pancreatic carcinoma (HPC) cells. These monoclonal antibodies, which recognize and bind to cell surface markers in HPC cells may be advantageously used for diagnosis and treatment of HPC.

In accordance with the present invention there are provided monoclonal antibodies which react specifically with antigenic markers on the surface of HPC cells. In accordance with a further aspect of the invention, there are provided hybridoma cell lines which produce monoclonal antibodies specifically reactive with HPC cell surface markers. Preferred hybridoma cell lines are those termed S3-41 and S3-53 identified by ATCC accession numbers HB 9318 and HB 9319, respectively, and the monoclonal antibodies produced by these cell lines.

It will be appreciated from the foregoing that the present invention provides novel markers for antibodies against HPC tumor cells. In one aspect of the invention, the monoclonal antibodies are used for in vitro immunoassays to detect HPC. In another aspect of the invention, the monoclonal antibodies, conjugated with certain detectable labels, are useful as in vivo imaging agents for detecting HPC. Moreover, when conjugated with certain toxins, such monoclonal antibodies are useful for therapeutic treatment of HPC.

Other features and advantages of the present invention will become apparent from the following detailed description which illustrates, by way of example, the principles of the invention.

BRIEF DESCRIPTION OF THE FIGURES

FIG. 3 shows reactivity of monoclonal antibodies with fresh-frozen humor tissue sections by immunoperoxidase staining.

FIG. 4 shows ELISA reactivity of monoclonal antibodies with cultured human cells.

FIG. 5 shows reactivity of monoclonal antibodies with fresh-frozen nonmalignant pathologic human tissue sections by immunoperoxidase staining.

FIG. 6 shows reactivity of monoclonal antibodies with fresh-frozen normal human tissue sections by immunoperoxidase staining.

DETAILED DESCRIPTION OF THE PREFERRED EMBODIMENT

I. DEFINITIONS

Figure 1:
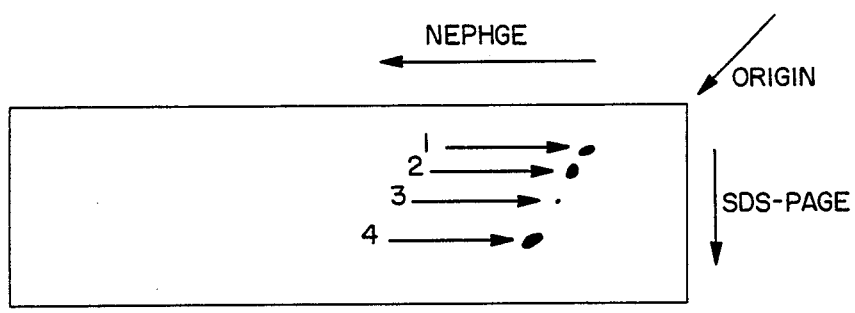
FIG. 1 shows two-dimensional gel analysis of immunoprecipitates obtained by reacting S3-41 (HB 9318) with radiolabeled extracts of FG cells.

"Monoclonal antibodies (Mabs) reactive with HPC" refers to homogenous populations of immunoglobulins which are capable of immunoreaction with antigens expressed on human pancreatic cancer (HPC) cells. It is understood that there may be a number of antigens present on the surface of any cell and, alternatively, that certain receptors present on HPC cells may also occur on other malignant or normal cell types. Moreover, such antigens may, in fact, have a number of antigenic determinants. The antibodies of the invention may be directed against one or more of these determinants. Any characteristic antigen associated with HPC may provide the requisite antigenic determinant.

Immunoglobulins, like all proteins, may exist in acidic, basic or neutral form depending on their amino acid composition and environment, and may be found in association with other molecules such as saccharides or lipids. The immunoglobulins of the present invention fall within the definition regardless of status in this regard as long as they remain capable of selectively reacting with HPC associated antigens.

"Cells" or "cell line" refers to the cells apparently denoted as well as the progeny thereof. It is known that during cell multiplication and growth cells or cell lines may not remain precisely constant in their genetic makeup and the progeny may, indeed, be distinguishable in some way from the parent cells. So long as the cells referred to herein retain the characteristic of secretion capability for Mabs reactive with HPC, as defined above, they are to be considered included in the definition.

"Immortalizing cell line" refers to a cell line which can be maintained perpetually, for practical purposes, in cell culture, i.e., for an indefinite number of transfers. It must also, when fused to an ordinary non-transformed cell line, which would normally not survive for more than a few days or weeks as a unicellular culture, be able to confer on the fusion product its own immortal properties.

GENERAL DESCRIPTION

The examples below describe the preparation of specific hybridoma cell lines producing monoclonal antibodies reactive with HPC cell antigens. It will be appreciated, however, that alternative methods may be employed to obtain alternative embodiments of the specific Mabs reactive with HPC cell antigens.

Techniques for preparing hybridomas are generally well-known in the art. Generally speaking, such hybridoma cell lines are prepared by a process involving the fusion under appropriate conditions of an immortalizing cell line and a B lymphocyte cell line appropriately immunized to produce the desired antibody. While the immortalizing cell lines so used are often of murine origin, those of any other mammalian species may be employed alternatively including those of rat, bovine, canine, human origin and the like. The immortalizing cell lines are most often of tumor origin, particularly myeloma cells, but may also include normal cells transformed with, for example, Epstein Barr Virus. Any immortalizing cell here may be used to prepare the hybridomas of the present invention.

Cells capable of secreting antibodies were employed as fusion partners, such as spleen cells or peripheral blood lymphocytes. The animal from which the cells were to be derived was immunized at intervals with whole cell suspensions of human pancreatic cancer cells. Alternatively, cell extracts or purified antigen may be used for immunization.

The immortalizing cells and lymphoid cells were fused to form hybridomas according to standard and well-known techniques employing polyethylene glycol as a fusing agent. Alternatively fusion may be accomplished by electrofusion. Hybridomas are screened for appropriate monoclonal antibody secretion by assaying the supernatant or protein purified from the ascites for reactivity with the desired cell or antigen. Such assay techniques include, among others, ELISA, RIA Western Blotting, or immunoprecipitation.

In the present invention, hybridomas were initially screened for production of antibodies reactive with HPC cells. Alternatively, HPC cell extracts or purified antigens could be used for screening. In order to further characterize the monoclonal antibodies, their reactivity with various HPC cell lines, other tumor cell lines and a variety of other normal, malignant and non-malignant pathological human tissues was determined using standard assay techniques such as ELISA, RIA, immunoprecipitation, histochemical staining procedures including indirect immunoperoxidase or indirect immunofluorescence staining. The hybridomas of the present invention were found to produce monoclonal antibodies generally highly reactive with all human pancreatic cell lines. They also displayed high reactivity with cells derived from other tumors, noticeably those of gastrointestinal and genitourinary tract origin. Moreover, although they displayed some reactivity with certain normal tissues, the Mab displayed negligible reactivity with major organs such as liver and kidney. Apparently, the antigens against which the antibodies are directed are highly expressed on HPC cells but only moderately or less on other cell types.

Because of their selective reactivity with HPC cell derived antigens the monoclonal antibodies are useful for both diagnosis and therapy of HPC and other carcinomas. Moreover, their nonreactivity with liver and kidney cells in particular permits them to be used therapeutically with relatively little risk of targeting these critical organs.

PARTICULAR EMBODIMENTS

The following examples illustrate a method for preparing hybridomas which can serve as sources for the desired monoclonal antibodies, and the antibodies thus produced. While the methods described are typical of those which might be advantageously used, other alternative procedures known to those skilled in the art may be alternatively employed. The examples are thus intended to illustrate, but not to limit the invention.

EXAMPLE I

PREPARATION OF HYBRIDOMA CELL LINE

Murine Mabs reactive with HPC cell lines were produced essentially according to the standard techniques of Kohler and Milstein, Nature 256:495 (1975). Briefly, standard HPC cell lines such as COLO 357 and its subclones were used to obtain the antigenic preparation. Preferably cells of the cell line termed FG were employed. (Kajiji, S. M., Intraneoplastic Diversity in Human Pancreatic Cancer, Ph.D. Thesis, Brown University (1984). Alternatively other pancreatic cell lines expressing the antigens may be used, such as BxPC-3 (ATCC No. CRL1687). The cells were grown in a monolayer culture and harvested by EDTA treatment. Briefly, confluent monolayers were incubated for 20 minutes at 37° C. with PBS containing 10 mM EDTA and 0.02% KCl. The detached cells were collected, centrifuged at 1000×g for 10 minutes and washed twice with cold PBS. Alternatively, cell suspensions were derived from FG xenografts grown in Balb/c athymic nude mice.

Two to four month old normal Balb/c mice were immunized with whole cell suspensions at weekly intervals with six intraperitoneal 0.5 ml injections, containing approximately $5 \times 10^6$ to $5 \times 10^8$ cells/injection/mouse. Three days after the final injection, the mice were sacrificed and the spleens removed. The spleens were placed in serum free Dulbecco's Minimal Essential Medium (DMEM) in separate Petri dishes and washed. The splenocytes were gently teased out of the fibrous splenic capsule using a rubber policeman. The cell suspension was then placed in a 15 ml tube and centrifuged at 1000×g for 10 minutes. The pellet was then washed twice with serum-free DMEM.

The washed spleen cells and the P3X63Ag8 myeloma cells were fused according to the method of Kohler and Milstein, supra. The immortalized cell line fusion partners used were the murine myeloma cell line P3X63Ag8 (ATCC Accession No. T1B9) These myeloma cells were grown at a density of $5 \times 10^5$ cells/ml and harvested by centrifugation at 1000×g for 10 minutes. The cell pellet was washed twice with serum free DMEM. Finally, the spleen cells and the P3X63Ag8 myeloma cells were combined at a ratio of 7:1 in a 50 ml tube and pelleted by centrifugation (1000 g for 10 minutes). The pellet was gently loosened and 1 ml of a 35% polyethylene glycol (PEG) solution was gently bubbled over the cells. After 1 minute, 1 ml of DMEM, containing 10% fetal calf serum (FCS)(Gibco, Grand Island, N.Y.) was added to the cell suspension and gently mixed.

The PEG was subsequently diluted by the addition of 10 ml DMEM containing 10% FCS and the cells were repelleted. The cell pellet containing hybridoma fusion products was resuspended in 30 ml hypoxanthine-aminopterin-thymidine (HAT) medium (aminopterin from Sigma Chemical Co., St. Louis, Mo.; hypoxanthine and thymidine from Calbiochem, La Jolla, Calif.). This cell suspension was then combined with 400 ml of HAT medium containing $2 \times 10^6$ thymocytes per ml (feeder cells). The contents were distributed into sterile 96 well plates (Costar, Cambridge, Mass.) and placed immediately in an incubator at 37° C. The spent media was replaced with fresh thymocyte containing HAT media after one week. Using this type of protocol successful hybridoma cultures were obtained which could be maintained with periodic addition of fresh DMEM containing 10% FCS.

Hybridomas producing monoclonal antibodies reactive with HPC cells were selected. After the cultures reached a cell density that covered 75-100% of the microtiter well surface, media from the hybridomas were screened for the presence of anti-HPC antibody, using a standard ELISA protocol. (Schultz, Cancer Res. 44:5914(1984)). Briefly, tumor cells dried onto the bottom of 96-well miniplates (Dynatech Microtiter Plates, American Scientific Products, McGaw Park, Ill.) were used as targets. The wells of antigen-coated 96 well plates to be used were rinsed with buffer A pH 8.0 (20 mM Tris, containing 150 mM NaCl, 0.2% Tween 20 and 0.01% Thimerosal). The hybridoma supernatant diluted 1:2 in buffer B (buffer A containing 0.1% bovine serum albumin) was added to the wells and incubated for 1 hour at room temperature to permit binding of specific antibodies. Specifically bound antibodies were detected by adding horseradish peroxidase-conjugated rabbit anti-mouse immunoglobulin (BioRad, Richmond, CA) to wells that were rinsed free of the excess hybridoma supernatant by washing with buffer A. After incubation for 1 hour at room temperature the secondary antibody was decanted, the wells washed with buffer A, and 50 μl/well of substrate solution (ten milliliters of 80 mM citrate phosphate buffer, pH 5.0 containing 4 mg O-phenylenediamine (Sigma Chem. Co., St. Louis, MO) and 4 μl 30% hydrogen peroxide) was added. The plates were incubated in the dark for 30 min at RT and the color reaction was stopped by adding 25 μl of 4M sulfuric acid to each well. Specifically-bound antibodies were detected by measuring the absorbance at OD 490 on an ELISA scanner C model EL310, Biotek Instruments Winooski, Vt.) within 30 min. Reactivity was graded as follows: $A_{490} \leq 0.15$, -; $A_{490} = 0.15$ to 0.3, 1+; $A_{490} = 0.3$ to 0.6, 2+; $A_{490} = 0.6$ to 1.2, 3+; $A_{490} \geq 1.2$, 4+. Hybridomas that were reactive with the immunizing FG cells but not with the lymphoblastoid 721-P cells were further screened for reactivity with frozen sections of HPC according to the procedure of Example II below. Only those that were reactive with frozen sections of HPC but not reactive with frozen sections of normal human liver, kidney and lung were selected. The two hybridoma cells lines selected for further study were designated S3-41 and S3-53, respectively.

EXAMPLE II

CHARACTERIZATION OF MONOCLONAL REACTIVITY

A. Reactivity with Human Tumor Tissues.

The reactivity of the monoclonal antibodies was determined by indirect immunoperoxidase staining as follows. Two- to 4-μm sections of frozen tissue blocks were cut on a cryotome, mounted on gelatin-coated glass slides, air-dried, and tested immediately in an indirect immunoperoxidase assay using the method of Taylor, Arch. Pathol. Lab. Med. 102:113 (1970). Briefly, after washing once in Hanks' balanced salt solution (Gibco, Grand Island, N.Y.) and phosphate buffered saline (PBS 10 mM sodium phosphate, 0.15M NaCl, pH 7.0), sections were incubated at room temperature sequentially with: diluting buffer (PBS containing 5% normal goat serum and 1% bovine serum albumin) for 15 min; a 1:2 dilution of hybridoma supernatants or appropriate isotype-matched controls for one hour; horseradish peroxidase-conjugated goat anti-mouse Ig antiserum (Bio-Rad, Richmond, Calif.) diluted 1:50 and containing 5% normal human serum for one hour; and finally substrate buffer (10 mM Tris, pH 7.4, 0.6 mg/ml 3,3'-diaminobenzidine, 0.015% $H_2O_2$) for 15 min. Washes with HBSS and PBS were performed between incubations. Sections were counterstained in 1% methylene blue, dehydrated through graded ethanol, washed in Histo-Clear (National Diagnostics, Somerville, N.J.), mounted in Pro-Texx (Lerner Laboratories, New Haven, Conn.), and examined by light microscopy.

FIG. 3 summarizes the reactivity of monoclonal antibodies produced by hybridoma cell lines S3-41 and S3-53 with 65 different tumors. As indicated, S3-41 was generally reactive only with carcinomas of the pancreas gastrointestinal tract, genitourinary tract, and head and neck tumors. Moreover, in virtually all instances, staining by the S3-41 Mabs was distinctly associated with the basement membranes surrounding tumor foci, producing a characteristic one-sided basal surface staining of cells at the epithelial stromal interface. In the few cases of lung carcinomas, melanoma and breast cancer tissues that were stained, reactivity was also confined to the basement membranes.

Mab S3-53 reacted with each of the seven pancreatic adenocarcinomas tested, including pancreatic carcinoma of the acinar cell type. Mab S3-53 displayed a wide range of reactivity among tumor tissues examined. Moreover, reactivity of S3-53 was generally intense with the majority of tumor cells within a tissue. Tumor cell basement membranes were also stained in some cases.

Reactivity with Human Cell Lines

The reactivity of Mabs against a panel of cell lines in culture was determined by ELISA reactivity, according to the Method of Schultz, Cancer Res. 44:5914 (1984), as detailed in Example I.

Cells dried onto the bottom of 96-well miniplates were used as targets for ELISA. Horseradish peroxidase-conjugated goat anti-mouse Ig antiserum (Bio-Rad, Richmond, CA) was used as the secondary antibody.

The reactivity of Mabs S3-41 and S3-53 is shown in FIG. 4. Both Mabs were reactive with the majority of the ten HPC cell lines tested. Moreover, both displayed particularly strong reactivity with cell lines derived from lung cancer, skin cancer and gastrointestinal and genitourinary tract tumors. S3-53 displayed moderate to strong positivity with tumor cell lines of neuroectodermal origin including melanoma, glioblastoma and neuroblastoma lines. Both antibodies were generally non-reactive with human red blood cells of blood types AB+, A+, B+, O+, and O−, normal diploid fibroblasts and leukemic or lymphoid cell lines.

C. Reactivity with Non-malignant Pathologic Human Tissues

The reactivity of the Mabs with a panel of inflammatory pancreases, benign tumor and hyperplastic epithelia was determined by indirect immunoperoxidase staining of frozen tissue sections, according to the method of section A, above. Both Mab S3-41 and Mab S3-53 showed some reactivity with the duct cells of chronic pancreatitis tissues. Mab S3-53 was widely reactive in that it stained every non-malignant pathologic tissue examined, although always in discrete areas. FIG. 5 shows the results of testing with this panel of tissues.

D. Reactivity with Normal Adult and Fetal Tissues.

The reactivity of the Mabs with fresh frozen normal adult and fetal tissues was determined by indirect immunoperoxidase staining according to the method of section A, above. The antibodies were unreactive with the vast majority of normal tissues examined. However, Mab S3-41 displayed some reactivity with the basal epithelial layers or basement membranes of the esophagus, cervix, and large intestine, plantar skin, breast tissue and ileal epithelium. The restricted expression of the S3-41 antigen by the proliferating cell layers of normal stratified epithelia and its localization at the epithelial stromal interface suggests that this molecule may be an early differentiation antigen (possibly involved in cell adhesion) of epithelial cells that is re-expressed following malignant transformation. Further, the S3-41 antigen may be useful for diagnosis and therapeutic intervention of other skin-related disorders such as psoriasis and basal cell carcinomas and may prove to be a valuable cell surface marker for investigating epidermal cell biology.

Mab S3-53 reacted with the acinar cells of adult and fetal pancreases, fetal pancreatic ducts, and the parenchyma and bile ducts of ⅓ livers that were tested. It was moderately reactive with the esophagus, stomach and small intestine, cervix, uterus, breast, fetal and adult lung parenchyma, fetal kidney, cerebral cortex, and with the molecular layers and Purkinje cells within the adult cerebellum. All layers of plantar skin including basement membrane were also intensely stained.

FIG. 6 summarizes the results of this panel of tests.

E. Reactivity with Cell Surfaces

To determine whether the antigens recognized by the Mabs were expressed on surface of cells of reactive tissues, viable HPC cells were tested with the Mabs in indirect immunofluorescence assays as follows:

Cells grown to confluence on glass cover slips were washed once with cold HBSS, overlaid with 0.1 ml of 1:2 hybridoma supernatant for one hour at 4° C., washed in cold HBSS, and overlaid with 0.1 ml of 1:50 fluorescein isothiocyanate-conjugated goat anti-mouse Ig antiserum (Tago, Burlingame, Calif.) for one hour at 4° C. After washing and fixing in 3% paraformaldehyde, cells were mounted in 80% glycerol, 1 mg/ml p-phenylenediamine, 200 mM Tris, pH 8.5, examined and photographed with a Zeiss fluorescence microscope.

Both Mab S3-41 and S3-53 showed distinct staining of the plasma membrane, indicating recognition of cell surface structures. Both stained the entire cell population, displaying a contiguous, linear membrane pattern.

EXAMPLE III

IMMUNOCHEMICAL CHARACTERIZATION OF ANTIGENS

In order to assess the chemical nature of the antigens recognized by Mabs, HPC cells were radiolabeled by incubation with either L-[$^3$H]-leucine or [$^3$H]-glucosamine, detergent solubilized and then subjected to immunoprecipitation with Mab immunosorbents, as follows:

Ten μl of a 10% suspension of protein-A-Sepharose (Pharmacia, Uppsala, Sweden) were incubated at 4° C. for 1 hour with 5 μl of rabbit anti-mouse Ig antibodies (Accurate Chemicals, Westbury, N.Y.) in 0.3 ml of PORT buffer (10 mM Tris, pH 8.5, 0.15 M Nacl, 0.5% Tween 20, 0.1% Renex 30, 2.5 mM sodium azide, 0.1% ovalbumin). After washing twice with PORT buffer, incubating 1 hour at 4° C. with 1 ml hybridoma supernatants and washing twice with PORT buffer, the beads were incubated overnight at 4° C. with radiolabeled cell extract ((1–2×10$^7$ cpm). The immunosorbents were washed 8 times with PORT buffer (10 mM Tris, pH 8.5, 0.15M NaCl, 0.5% Tween 20, 0.1% Renex 30, 2.5 mM sodium azide) and bound antigens were eluted in Laemmli buffer (Nature 227:680(1970)). The samples were analyzed by SDS-PAGE on slab gels and visualized by fluorography.

Results of the SDS-PAGE analysis indicated that Mab S3-41 recognized a doublet protein antigen, of 205 kD and 135 kD, respectively. Both bands were glycosylated as they incorporated [$^3$H]-glucosamine. In some cases two additional bands of 150 kD and 185 kD were also seen. A band of 116 kD co-precipitated with S3-41 bands, but was non-specific since it could be removed by preabsorption with control immunosorbents. Mab S3-53 recognized a highly glycosylated 140 kD protein. Comparison of electrophoresis under reducing and non-reducing conditions indicated that none of the bands were disulfide bridged and is further discussed under IV a. and V a. below.

Immunoprecipitation of a metabolically labeled HPC indicated that the antigenic determinants recognized by each of the monoclonals are carried by protein molecules. These proteins are also glycosylated, so that it remains to be determined whether the recognized epitopes are expressed by the protein or the glycan part of these molecules. On the basis of their tissue distribution and molecular weights, the HPC-associated antigens we describe herein do not show any obvious resemblance to any other antigens known to have been previously reported in the literature.

EXAMPLE IV

ADDITIONAL BIOCHEMICAL CHARACTERISTICS OF S3-41 ANTIGEN a. Molecular profile under non-reducing conditions:

The results obtained by indirect immunoprecipitation of detergent extracts of pancreatic cancer cells that were intrinsically radiolabeled with either [$^{35}$S]-methionine or [$^3$H]-glucosamine and their subsequent analysis by SDS-PAGE under nonreducing conditions revealed that S3-41 antigen migrates as two bands of 185 kD and 150 kD, respectively.

b. Extrinsic radiolabeling with $^{125}I$

Molecules present on the surface of FG pancreatic cancer cells were labeled using the Enzymobead radioiodination reagent (Bio-Rad, Richmond, Calif.). Briefly, confluent monolayers were washed with PBS to remove serum proteins, and iodinated for 15 mins at RT. The iodination reaction was quenched by transferring the flasks to 4° C., rinsing the monolayers with cold PBS and lysing the cells with RIPA lysis buffer. The lysate was clarified by centrifuging for 15 mins. at 4° C. in an Eppendorf centrifuge. Freshly iodinated lysates were generally used for immunoprecipitation studies. S3-41 precipitates radiolabeled molecules that migrate on SDS-PAGE as a single species of 205 kD.

c. Metabolic labeling of FG cells

Exponentially-growing monolayers were used in order to intrinsically label the cells with either $[^{32}P]$-orthophosphate or $[^{35}S]O_4$.

In the former case, monolayers were washed twice with 50 mM HEPES containing 0.1% BSA. The cells were then propagated for 15 minutes in phosphate free medium (Irvine Scientific, Santa Ana, Calif.) and then pulsed with 0.5 mCi per T-75 flask of $[^{32}P]$-orthophosphate (8 mCi/ml, carrier free) for 3 hours at 37° C. After labeling, the cells were washed twice with cold PBS containing 100 mM sodium pyrophosphate, 100 mM sodium fluoride, 4 mM EDTA and then solubilized by being held for 10 min on ice in RIPA lysis buffer containing 100 mM sodium pyrophosphate, 100 mM sodium fluoride, 4 mM EDTA and 2 mM PMSF.

S3-41 precipitated a molecule with apparent mobility in SDS-PAGE of 205 kD.

For labeling with $[^{35}SO_4]$, the cells were incubated for one hour at 37° C. in $SO_4$-free medium (modified DMEM lacking cysteine but containing 10 μg/ml insulin, 10 μg/ml transferrin, 0.172 μg/ml Na selenite, 0.3 μg/ml methionine, 1 μg/L glucose, 1 mM magnesium chloride, 2 mM calcium chloride ($CaCl_2$), 6 mM KCl, 0.15M NaCl, 1 mM sodium phosphate (monobasic) 0.15% sodium bicarbonate and 0.0005% phenol red) and then pulsed with 2 mCi/T-75 flask of $[^{35}SO_4]$ for 6 hours at 37° C. The labeled cells were then detached using PBS containing 10 mM EDTA and 0.02% KCl, washed twice with Tris buffer, pH 7.5 and lysed on ice in RIPA lysis buffer.

The cell lysates in both cases were cleared by ultracentrifugation at 100,000×g for 45 min and stored at −70° C. for use in indirect immunoprecipitation studies. S3-41 precipitates molecules with apparent mobility in SDS-PAGE of 205 kD and 135 kD, respectively.

d. Metabolic labeling with $[^{35}S]$-methionine in the presence of Tunicamycin

Indirect immunoprecipitation with Mab S3-41 of detergent lysates of cells intrinsically labeled with $[^{35}S]$-methionine in the presence of tunicamycin (an inhibitor of N-linked glycosylation) and subsequent analysis by SDS-PAGE under reducing conditions revealed the presence of two major bands of 190 kD and 100 kD, respectively.

Semiconfluent cultures of FG cells were incubated for 10-12 hours at 37° C. with 1 μg/ml tunicamycin. The cells were then pulsed for an additional 12 hours with 1 mCi $[^{35}S]$-methionine in methionine-free RPMI medium containing 3% FCS and 1 μg/ml tunicamycin. Control flasks, similarly labeled with $[^{35}S]$-methionine in the absence of tunicacymin, were also prepared. The metabolically-labeled cells were then harvested as previously described and lysed using RIPA lysis buffer. Cell lysates were clarified by centrifugation at 100,000×g for 45 min at 4° C. and subsequent storage was at −70° C.

e. Two-dimensional gel analyses

Immunoprecipitations were carried out by overnight incubation of cell lysates with immunoabsorbents prepared by activated CNBr conjugation of Mab to Sepharose 4B-CL beads (Pharmacia, Uppsala, Sweden). After elution in 8M urea at room temperature, samples were analyzed by two-dimensional electrophoresis, consisting of nonequilibrium pH electrophoresis on tube gels in the first dimension, followed by SDS-PAGE on 7.5% acrylamide slab gels. Gels were impregnated with 2, 5,-diphenyloxazole, dried and exposed for the indicated times to Kodak XAR-5 X-ray film at −70° C. The resulting pattern of migration is shown in FIG. 1.

f. Treatment of S3-41 antigen with glycolytic enzymes

In some experiments, washed immunoprecipitates were resuspended in 50 l of PBS, pH 7.2 with or without the addition of 0.5–1.0 U Neuraminidase (*Arthrobacter ureafaciens*) (Calbiochem, La Jolla, Calif.) and incubated for varying times at 37° C. Fifty microliters of the 2× Laemmli sample buffer was then added and the samples were analyzed by SDS-PAGE. Similarly, some washed immunoprecipitates were incubated with 50 μl of PBS, pH 7.2, containing 0.5 U of purified Endo neuraminidase (gift from F. Troy, U.C. Davis) for 6–12 hours at 37° C.

Treatment of immunoprecipitates with endoglycosidases H (Boehringer Manheim Biochemicals, Indianapolis, Ind.) and F (gift from J. Elder, Scripps Clinic and Research Foundation, La Jolla, Calif.) and PNGase (gift from A. Varki, U.C.S.D. Cancer Center, San Diego, Calif.) was performed in the following way. The antigens immunoprecipitated by the immunosorbents were solubilized by boiling the washed immunoprecipitates for 3 minutes in 10 μl of 0.5% SDS and 0.05M beta-2-mercaptoethanol. The samples were cooled by placing the tubes on ice, and then diluted 100-fold with PBS, pH 7.2. Treatment with Endo F and PNGase required the addition of PBS containing 50 mM EDTA and 1% NP-40. Varying concentrations of the enzymes were added and digestion was allowed to proceed for 12–18 hours at 37° C. After incubation, 20 μl of 5X sample buffer was added to the reaction mixture and the samples were analyzed by SDS-PAGE. The glycolytic enzymes characteristically modify the apparent mobility of immunoprecipitated antigens in SDS-PAGE, by removing discrete portions of O-linked or N-linked glycans. The results obtained for S3-41 antigen can be summarized as follows:

| Enzyme | Apparent m.w. | |
| --- | --- | --- |
| Endo F | 190 kD | 100 kD |
| PNGase | 190 kD | 100 kD |
| Endo H | 205 kD | 126 kD |
| Neuraminidase | 126 kD | 98 kD |
| *Endo neuraminidase* | 135 kD | 150 kD | g. Binding to lectins

When radiolabeled lysates were preabsorbed with lentil lectin-agarose beads (Vector Labs, Burlingame, Calif.), the antigens reactive with S3-41 were removed. Removal of antigen was shown by immunoprecipitation of bead supernatant, followed by SDS-PAGE. Similar treatment of radiolabeled lysates with wheat germ agglutinin-agarose beads (E.Y. Labs., San Mateo, Calif.) did not remove the S3-41 antigen. Therefore, the antigen reactive with S3-41 was characteristically bound to lentil lectin, but not to wheat germ agglutinin.

EXAMPLE V
ADDITIONAL BIOCHEMICAL CHARACTERISTICS OF S3-53 ANTIGEN a. Molecular profile under non-reducing conditions The method follows that of Example IV a, using S3-53 in place of S3-41. S3-53 antigen migrates as a single band of 125 kD under non-reducing conditions.

b. Extrinsic Radiolabeling with $^{125}I$

The method follows that of Example IV b, using S3-53 in place of S3-41. S3-53 precipitates radiolabeled molecules that migrate on SDS-PAGE as a single species of 140 kD.

c. Metabolic labeling of FG cells

The method follows that of Example IV b, using S3-53 in place of S3-41. In both cases, S3-53 precipitates molecules with mobility in SDS-PAGE of 140 kD.

d. Metabolic labeling with $[^{35}S]$-methionine in the presence of Tunicamycin

The method follows that of Example as IV d, using S3-53 in place of S3-41. S3-53 immunoprecipitated a single band in SDS-PAGE of 100 kD.

e. Two-dimensional gel analysis

Figure 2:
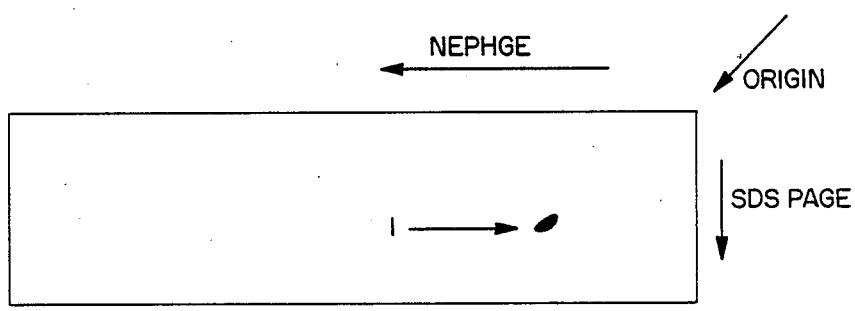
FIG. 2 shows two-dimension gel analysis of immunoprecipitates obtained by reacting S3-53 (HB 9319) with radiolabeled extracts of FG cells.

The method follows that of IV e using S3-53 in place of S3-41. The resulting pattern of migration is shown in FIG. 2.

f. Treatment with glycolytic enzymes

The method follows that of IV f using S3-53 in place of S3-41. The antigen recognized by S3-53 is isolated by immunoprecipitation of radiolabeled cell lysates. The immunoprecipitates are treated with a variety of exoglycolytic and endoglycolytic enzymes. After treatment the apparent mobility of the precipitated antigens is determined in a SDS-PAGE system. The glycolytic enzymes characteristically modify the apparent molecular weight of the S3-53 antigens, by removing discrete portions of O-linked or N-linked glycans. The results obtained can be schematically summarized as follows:

| Enzyme | Apparent m.w. |
|---|---|
| Endo F | not determined |
| PNGase | not determined |
| Endo H | 140 kD |
| Neuraminidase | 135 kD |
| Endo neuraminidase | 140 kD | g. Binding to lectins

The method follows that of IV g, using S3-53 in place of S3-41. When radiolabled lysates were preabsorbed with lentil lectin-agarose beads, the antigens reactive with S3-53 were removed. When they were preabsorbed with wheat germ agglutininagarose beads, the antigens were not removed. Removal of antigen was shown by immunoprecipitation of bead supernatant, followed by SDS-PAGE. Therefore, the antigen reactive with S3-53 characteristically binds to lentil lectin, but not to wheat germ agglutinin.

h. Biosynthesis of S3-53 antigen

The method is as described in IV i. Pulse-chase biosynthetic studies revealed the presence of a precursor molecule of 120 kD after a 10 minute pulse with $[^{35}S]$-methionine. At the 15 minute time point of chase small amounts of the 140 kDa S3-53 antigen were also visible. Both of these molecules were observed to be present until 60 minutes after chase. However, only the 140 kD molecule was detectable at 4 hours after chase until 20 hours after chase. Thus, the 120 kD component serves as a precursor for the 140 kD component of the S3-53 antigen.

EXAMPLE VI
THERAPEUTIC TREATMENT OF HPC

Patients determined to have HPC are treated with monoclonal antibodies reactive with HPC cells and conjugated with a toxin such as ricin, or any cytotoxic drug. The monoclonal antibody conjugates are administered (intravenously, intramuscularly, intraperitoneally, or the like, in a physiologically acceptable carrier solution, such as phosphate buffered saline. The dosage is determined by the body weight of the host, it preferably being in the range of about 0.1 mg/kg to about 40 mg/kg body weight, and usually about 1 mg/kg to about 10 mg/kg of host body weight. Alternatively, the dosage is established by evaluating the extent of the tumor as by quantitatively standardized ELISA, radioimaging or other methods. Treatment is repeated at intervals as necessary, to effect enhancement of the host's ability to recover from the infection.

EXAMPLE VII
IMAGING OF HPC TUMOR

Monoclonal antibodies reactive with HPC cells are utilized to determine the location and extent of HPC by methods well-known in the art, for example, Larson et al., Journal of Clinical Investigation 72:2101 (1983), which is incorporated by reference. Monoclonal antibodies are preferably radiolabeled by radioiodination or by other radiolabeling techniques well known in the art, such as chelation using a chelating agent such as diethylenetriaminepenta-acetic acid (DTPA); or are otherwise labeled, such as with agents having paramagnetic properties, with chemiluminescent substrates, or with components of an enzymatic reaction. The radiolabeled monoclonal antibodies are purified and formulated for pharmaceutical use. A solution of the labeled monoclonal antibodies in a carrier, for example in phosphate buffered saline, is injected intravenously into a host. The appropriate dose is in the range of about 100 μg to 50 mg. Time is permitted for the antibodies to migrate to regions of the body having concentrations of cells with antigenic determinants reactive therewith. Concentrations of radioisotypes in certain tissues are determined or may be mapped either by techniques of whole body imaging which are well-known in the art, (See, for example, Rainsbury et al., Lancet Oct. 22, 1983, 934 (1983)) which is incorporated by reference, or by evaluating biopsied tissue or extracted body fluid using a scintillation counter. Where non-radioactive labels are used, other appropriate monitoring means are employed, such as a detector of nuclear magnetic resonance or a spectrophotometer. Areas of high radiation levels are indicative of the presence of cells such as HPC, having the cell surface markers of the present invention.

We claim:

1. A monoclonal antibody preparation reactive with the basement membranes surrounding tumor foci at the epithelial stromal interface which has the binding characteristics of S3-41 as set forth in FIG. 3.

2. The monoclonal antibody preparation of claim 1 which further has the reactivity pattern of S3-41 as set forth in FIGS. 4-6.

3. The monoclonal antibody preparation of claim 2 which is S3-41.

4. A monoclonal antibody preparation of reacts with tumor tissue according to the pattern shown for S3-53 in FIG. 3.

5. The monoclonal antibody preparation of claim 4 which further has the reactivity pattern shown for S3-53 in FIGS. 4-6.

6. The monoclonal antibody preparation of claim 5 which is S3-53.

7. A hybridoma cell line capable of secreting the monoclonal antibody preparation of claim 1.

8. The hybridoma of claim 7 which is S3-41.

9. A hybridoma cell line capable of secreting the monoclonal antibody preparation of claim 4.

10. The hybridoma of claim 7 which is S3-53.

* * * * *

UNITED STATES PATENT AND TRADEMARK OFFICE
CERTIFICATE OF CORRECTION

PATENT NO. : 4,962,048

DATED : October 9, 1990

INVENTOR(S) : Kajiji, et al.

It is certified that error appears in the above-identified patent and that said Letters Patent is hereby corrected as shown below:

In Column 1, line 7, insert:

--This invention was made with government support under Contract No. 1R01 CA47858 awarded by the National Institutes of Health. The government has certain rights in the invention.--

Signed and Sealed this

Twenty-third Day of April, 1996

Attest:

BRUCE LEHMAN

Attesting Officer

Commissioner of Patents and Trademarks